(12) United States Patent
Marshall

(10) Patent No.: US 10,092,433 B2
(45) Date of Patent: Oct. 9, 2018

(54) SUPPORT

(75) Inventor: Wesley Marshall, Broxbourne (GB)

(73) Assignee: Epiphany Innovations Limited, Hoddesdon (GB)

( * ) Notice: Subject to any disclaimer, the term of this patent is extended or adjusted under 35 U.S.C. 154(b) by 481 days.

(21) Appl. No.: 14/009,024

(22) PCT Filed: Mar. 28, 2012

(86) PCT No.: PCT/GB2012/000281
§ 371 (c)(1),
(2), (4) Date: Jan. 15, 2014

(87) PCT Pub. No.: WO2012/131298
PCT Pub. Date: Oct. 4, 2012

(65) Prior Publication Data
US 2014/0128788 A1 May 8, 2014

(30) Foreign Application Priority Data

Mar. 31, 2011 (GB) .................................. 1105514.2

(51) Int. Cl.
A61F 5/01 (2006.01)
A61F 5/02 (2006.01)
A61F 5/32 (2006.01)

(52) U.S. Cl.
CPC ................ *A61F 5/01* (2013.01); *A61F 5/024* (2013.01); *A61F 5/028* (2013.01); *A61F 5/32* (2013.01)

(58) Field of Classification Search
CPC .. A61F 5/024; A61F 5/028; A61F 5/32; A61F 5/01–5/0104; A61F 5/0193;
(Continued)

(56) References Cited

U.S. PATENT DOCUMENTS 2,652,051 A * 9/1953 Hoover ..................... A61F 5/24
128/100.1
2,733,712 A * 2/1956 Wuesthoff ............... A61F 5/028
128/96.1

(Continued)

FOREIGN PATENT DOCUMENTS

DE 3617807 A1 1/1987
EP 2036520 A1 3/2009
(Continued)

Primary Examiner — Victoria J Hicks
Assistant Examiner — Michelle J Lee
(74) Attorney, Agent, or Firm — Renner, Otto, Boisselle & Sklar, LLP

(57) ABSTRACT

A support for the trunk or a limb or joint of a human or animal comprises a first band having first and second end portions with respective fasteners which can be fastened together to fix the band in a loop around the trunk or a limb or joint and at least one pad located inwardly of the first band for engaging a surface portion of the trunk or a limb or joint. The second band has a portion located inwardly of the first band and supports said at least one pad for movement independently of the first band when the first band is fixed to apply pressure to said surface portion. An adjustment means is connected to the second band and extends from an inner side to an outer side of the first band to allow operation outwardly of the first band when the first band is fixed for adjusting the position of said at least one pad.

18 Claims, 21 Drawing Sheets

(58) Field of Classification Search
CPC ....... A61F 5/02–5/03; A61F 5/24–5/34; A61F 13/00; A61F 13/00004; A61F 13/00021
USPC .......... 602/19, 75–77; 128/96.1, 99.1; 2/44, 2/467, 464, 92
See application file for complete search history.

(56) References Cited

U.S. PATENT DOCUMENTS

| | | | | |
|---|---|---|---|---|
| 4,616,639 | A | * | 10/1986 | Huber ....................... A61F 5/01 128/99.1 |
| 4,715,364 | A | | 12/1987 | Noguchi ....................... 128/96.1 |
| 5,387,183 | A | * | 2/1995 | Jones ....................... A61F 5/028 128/100.1 |
| 5,586,969 | A | * | 12/1996 | Yewer, Jr. ............... A61F 5/028 128/101.1 |
| 2003/0187375 | A1 | | 10/2003 | Gaylord |
| 2005/0059917 | A1 | | 3/2005 | Garth ............................. 602/19 |
| 2010/0121240 | A1 | | 5/2010 | Smith ............................. 602/19 |
| 2011/0077567 | A1 | | 3/2011 | Bledsoe .......................... 602/19 |

FOREIGN PATENT DOCUMENTS

| | | | |
|---|---|---|---|
| GB | 956754 | A | 4/1964 |
| GB | 1256962 | A | 12/1971 |
| NL | 6906191 | A | 10/1969 |

* cited by examiner

SUPPORT

CROSS REFERENCE TO RELATED APPLICATIONS

The present application is a U.S. National Phase of PCT Patent Application No. PCT/GB2012/000281, filed Mar. 28, 2012, and claims priority to Great Britain Patent Application No. 1105514.2, filed Mar. 31, 2011, all of which are incorporated herein by reference in their entirety for all purposes.

This disclosure relates to supports. More particularly it relates to improved supports for the trunk or a limb or joint of a human or animal. As explained below in relation to specific embodiments of support, the support may serve as an orthotic device to assist in isolating and/or reducing the load or stretch of an area of injured soft tissue.

The literature is replete with proposals for support for the trunk or a limb or joint of humans and animals and for devices adapted to relieve, offload or unload stress. Many such supports and orthotic devices are expensive, complicated and difficult to adjust. Often devices must be provided in a wide range of different sizes or be bespoke made.

The present disclosure has arisen from our work seeking to provide supports that are relatively simple in construction, relatively inexpensive to produce, and readily adjustable by medical personnel or even by the user themselves, in many cases by the use of one hand.

In accordance with a first aspect of the present invention, a support for the trunk or a limb or joint of a human or animal comprising: a first band having first and second end portions with respective fasteners which can be fastened together to fix the band in a loop around the trunk or a limb or joint: at least one pad located inwardly of the first band for engaging a surface portion of the trunk or a limb or joint; a second band having a portion located inwardly of the first band and supporting said at least one pad for movement independently of the first band when the first band is fixed to apply pressure to said surface portion; and adjustment means connected to the second band and extending from an inner side to an outer side of the first band to allow operation outwardly of the first band when the first band is fixed for adjusting the position of said at least one pad.

The second band may comprise an elastic portion which is lengthwise extendible to allow movement of said at least one pad by operation of the adjustment means.

The adjustment means may be formed by a portion of the second band extending outwardly from the inner side to the outer side of the first band that can be tensioned to adjust the position of said at least one pad, the outwardly extending portion comprising a fastening for fastening to the first band for fixing the position of said at least one pad after tensioning.

Tensioning the outwardly extending portion of the second band may extend the elastic portion causing movement of said at least one pad for applying pressure to the surface portion of the trunk or a limb or joint.

Prior to fixing the first band, tensioning the outwardly extending portion may extend the elastic portion causes movement of said at least one pad such that the outwardly extending portion can be fixed to the first band with the elastic portion in a tensioned condition, and wherein when the first band is fixed to the trunk or a limb or joint, the outwardly extending portion can be unfixed from the first band to allow the elastic portion to contract thereby causing movement of said at least pad and applying pressure to the surface portion of the trunk or a limb or joint.

At least two pads may be located inwardly of the first band for engaging a surface portion of the trunk or a limb or joint, said second band supporting at least one of the pads for movement relative to the other of the pads independently of the first band to apply pressure to said surface portion between the pads, the adjustment means being operable outwardly of the first band when the first band is fixed for adjusting the spacing between the pads.

The adjustment means may extend from an inner side to an outer side of the first band through an aperture in the first band.

The second band may support a second of said pads inwardly of the first band for movement relative to the first band, and the adjustment means comprises a second outwardly extending portion for extending from the second band from an inner side to an outer side of the first band to allow operation outwardly of the first band when the first band is fixed for adjusting the spacing between the pads.

The first and second pads may be supported respectively by two said second bands and the adjustment means is formed by portions of the second bands extending from an inner side to an outer side of the first band that can be tensioned to adjust the spacing between the pads, the outwardly extending portions comprising respective fastenings for fastening to the first band for fixing the spacing between the pads after tensioning.

Prior to fixing the first band, tensioning the outwardly extending portions of the two second bands may extend the elastic portions and increase the spacing between the pads such that the outwardly extending portions can be fixed to the first band with the elastic portions in a tensioned condition, and wherein when the first band is fixed to the trunk or a limb or joint, the outwardly extending portions can be unfixed from the first band to allow the elastic portions to contract thereby decreasing the spacing between the pads and applying pressure to the surface portion of the trunk or a limb or joint.

The pads may be connected one to the other by a resilient clip which biases the pads towards each other, and tensioning the second band causes pads to move away from one another such that prior to fixing the first band, the second band can be tensioned to move the pads away from each other and the spacing between the pads fixed by fastening ends of the second band to the first band, wherein following fixing of the first band around the trunk or a limb or joint, the second band can be unfastened such that the pads move towards each other under the biasing force of the clip independently from the first band to apply pressure to a surface portion of the trunk or a limb or joint.

The adjustment means may comprise a wheel fixed for rotation relative to the first band and having a shaft that extends through an aperture in the first band to cooperate with the second band, wherein rotation of the wheel causes linear movement of the or each pad supported by the second band.

In another arrangement, the adjustment means comprises a cord extending through an aperture in the first band and connected to the or each of the second bands and a clamp for clamping the or each cord relative to the first band when the cords have been tensioned.

One or more retainers may be fixed to an inner surface of the first band for limiting movement of the second relative to the first band in a widthwise direction of the first band.

One or more of the pads may be arranged relative to the first band such that when the first band is fixed around the trunk or a limb or joint the pads remain visible to facilitate positioning of the pads.

One or more of the pads may be detachably mounted to the second band or the first band to allow movement of the pads prior to fixing the first band around the trunk or joint or limb and variation of the initial spacing between the pads.

In another aspect, the present invention provides a support for the trunk or a limb or joint of a human or animal comprising: a first band having first and second end portions with respective fasteners which can be fastened together to fix the band in a loop around the trunk or a limb or joint; at least one pad located inward of the first band for engaging a surface portion of the trunk or a limb or joint, the first band having an elastic portion which is lengthwise extendible so that tensioning the elastic portion causes movement of said at least one pad; a rigid spacer having at least one fastening for fastening outwardly to the first band for fixing the position of said at least one pad after the elastic portion is tensioned; wherein releasing the second band from the first band when the first band is fixed around a trunk or a limb or joint causes movement of said at least one pad under the bias of the elastic portion thereby applying pressure to a surface portion of the trunk or a limb or joint.

Reference may now be made to the description of preferred embodiments by way of example only with reference to the accompanying drawings, in which.

Figure 1:
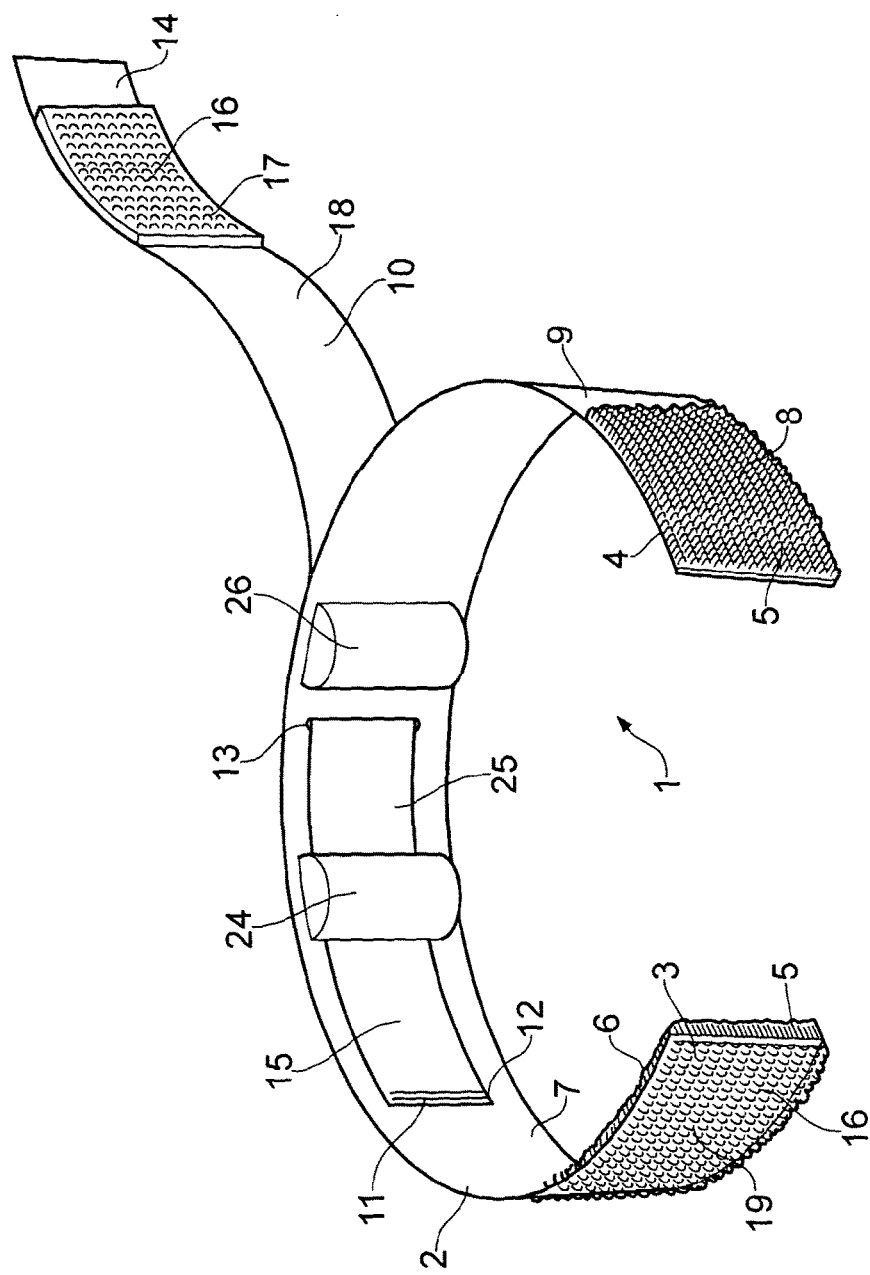
FIG. 1 is a perspective view of an embodiment of support produced in accordance with the teachings of this disclosure.
Figure 2:
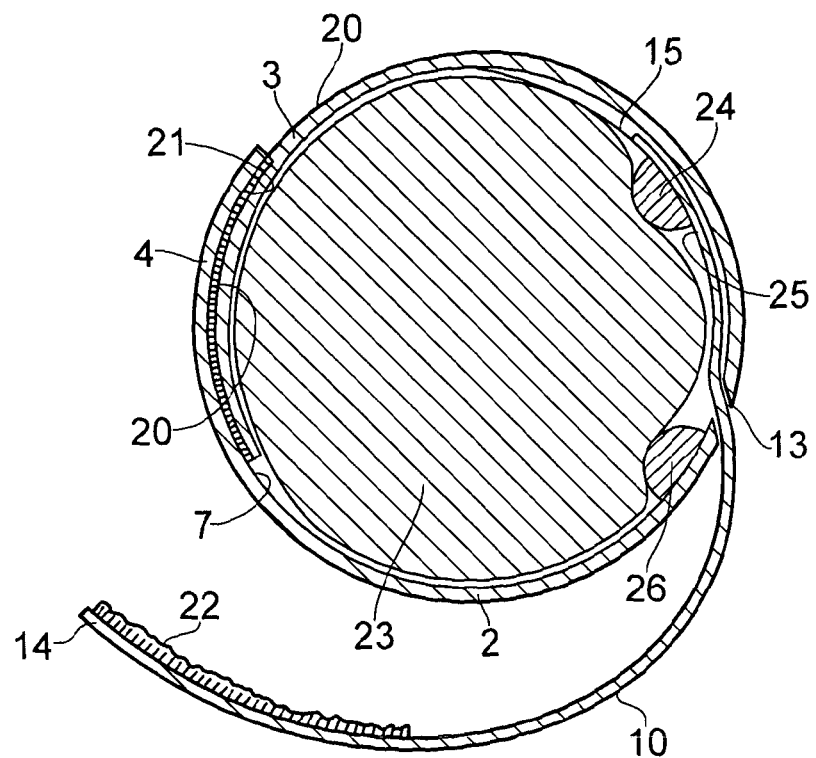
FIGS. 2 and 3 show a variation of the support of FIG. 1 in a sectional view through the support and a limb use to offload stress in the soft tissue of a limb, FIG. 2 showing the situation before fastening of the second band and FIG. 3 after doing so.
Figure 3:
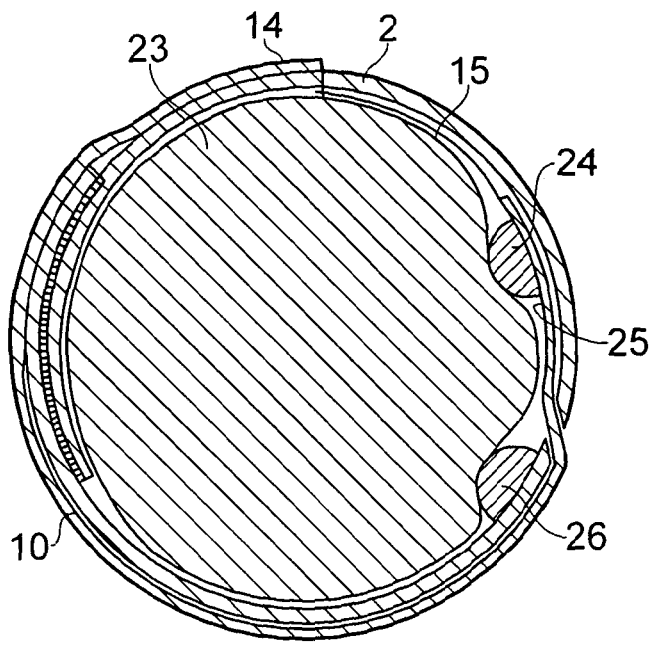
Figure 4:
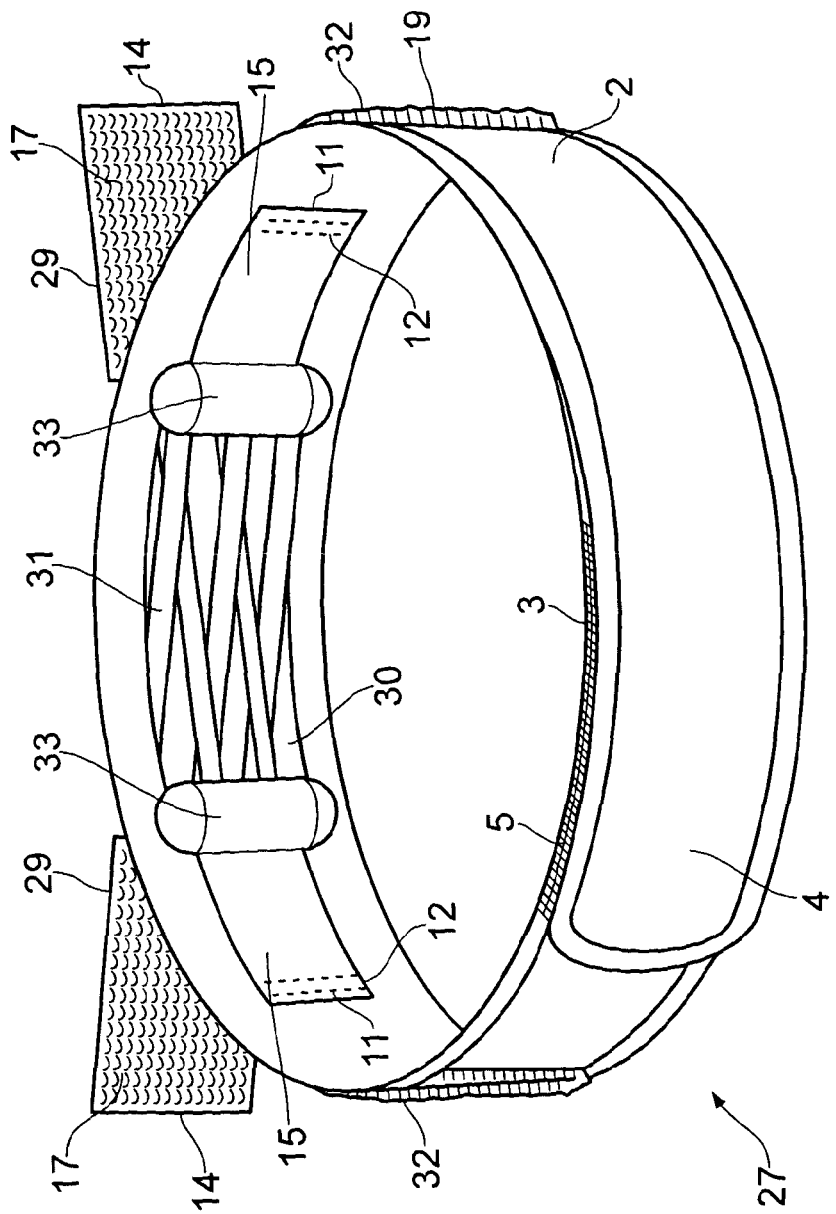
FIG. 4 is a perspective view of a second embodiment of support involving a pair of second bands and adapted for use as a lumbar support, with the ends of the first band fastened together.
Figure 5:
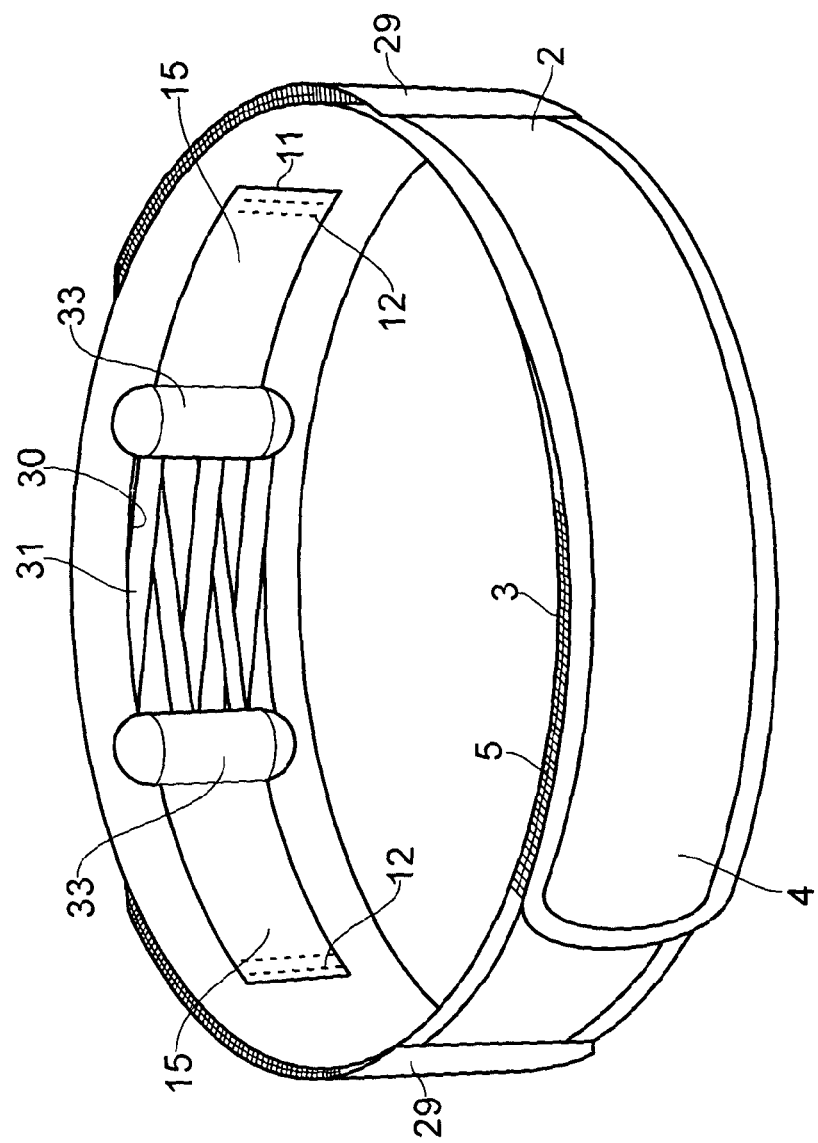
FIG. 5 is a view similar to FIG. 4 showing the support in use, but with the trunk omitted to enable details of the support to be seen, after pulling of the distal ends of the second bands and fastening of the same to the second side of the first band.
Figure 6:
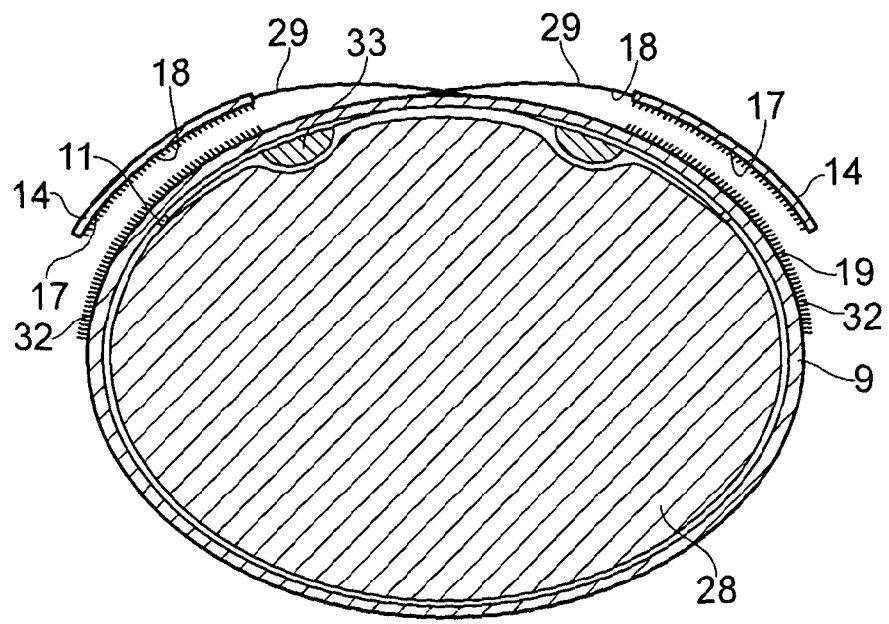
Figure 7:
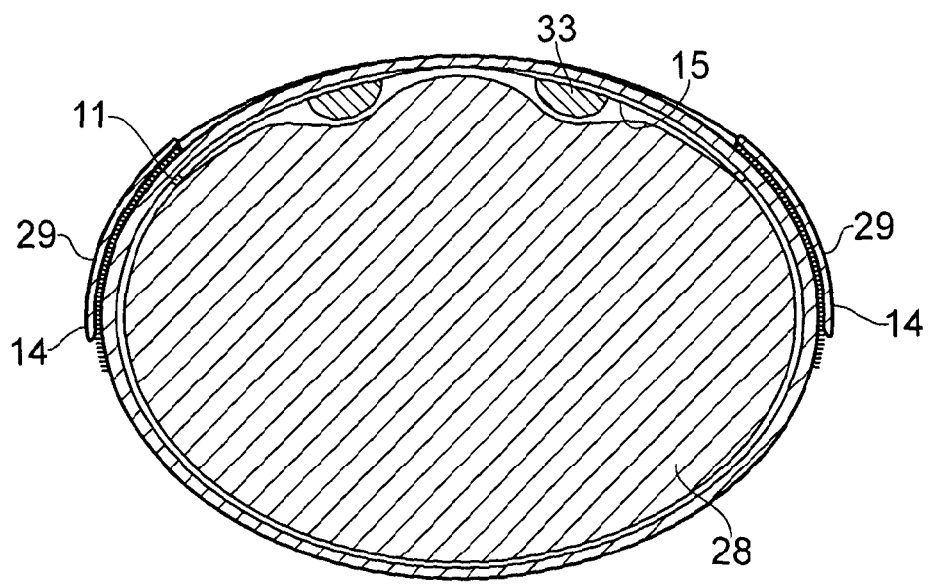
Figure 8:
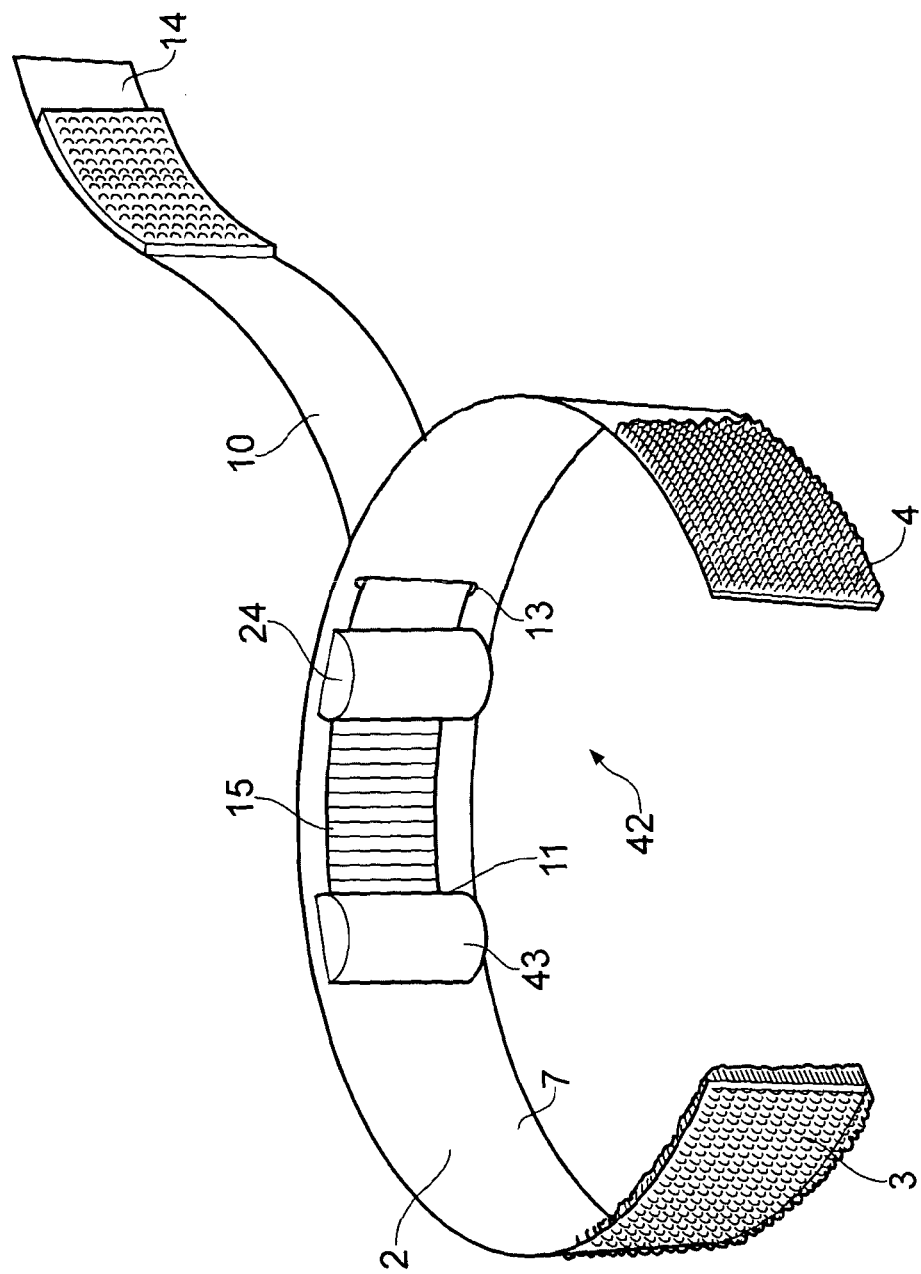
Figure 9:
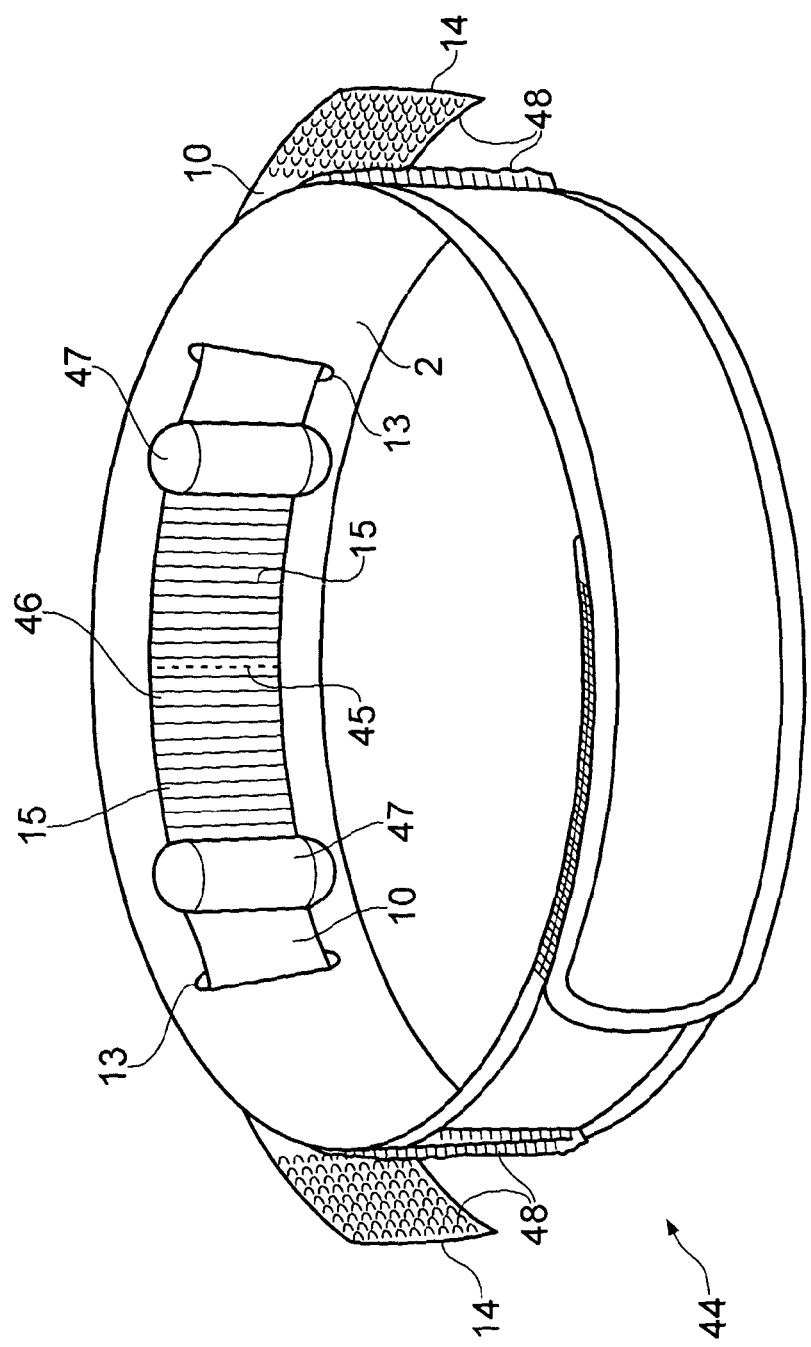
Figure 10:
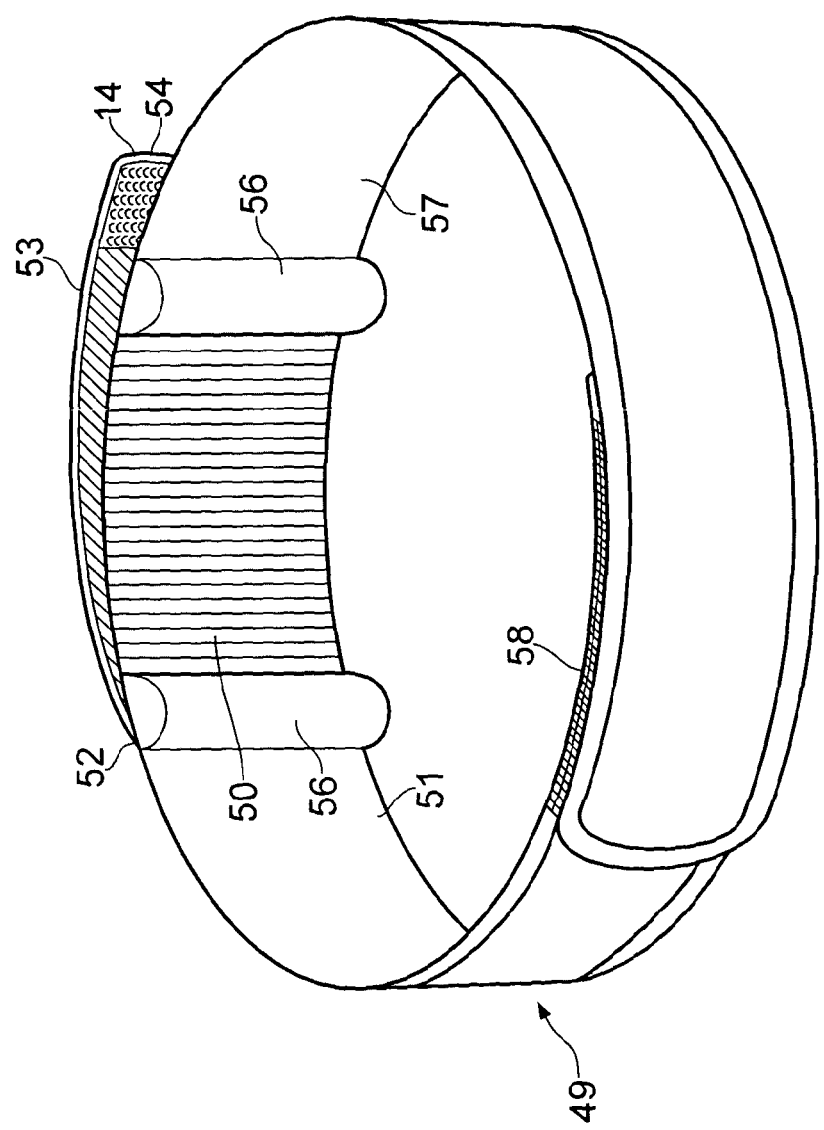
Figure 12A:
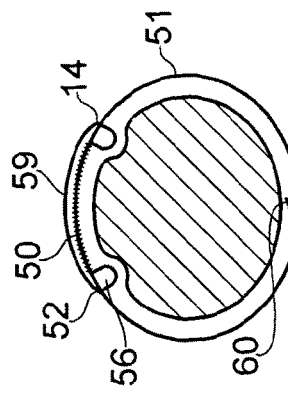
Figure 12B:
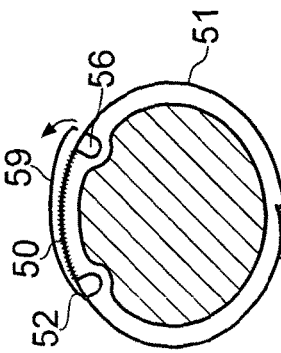
Figure 12C:
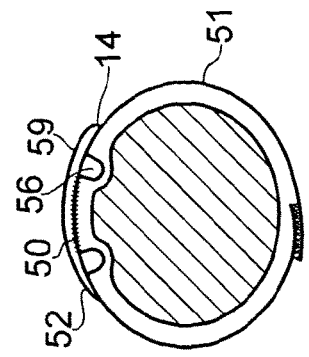
Figure 11:
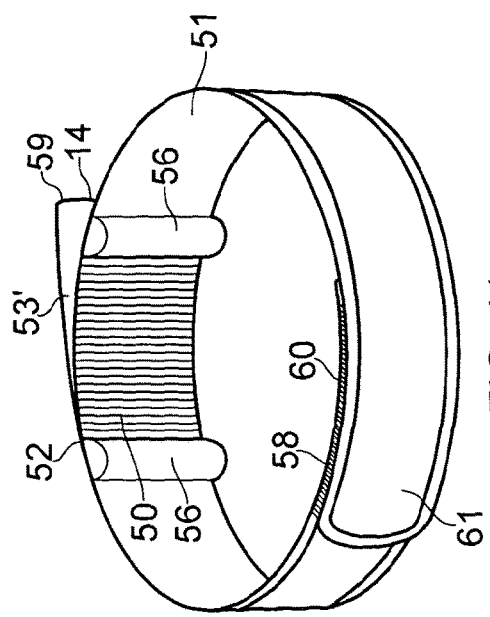
Figure 13A:
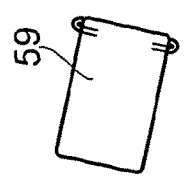
Figure 13B:
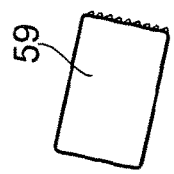
Figure 13C:
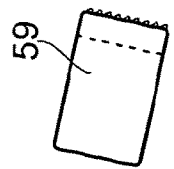
Figure 14:
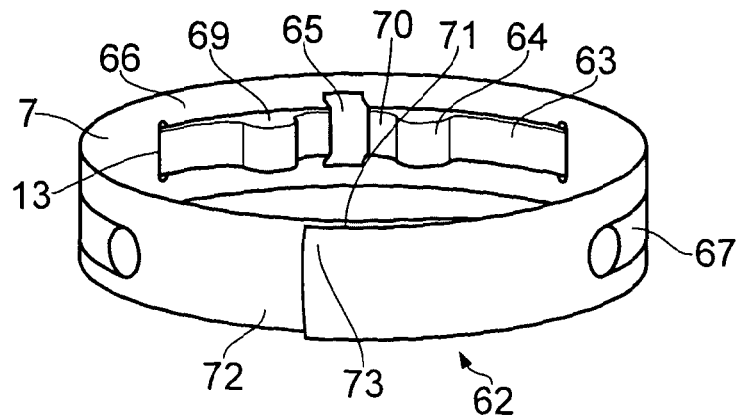
Figure 15A:
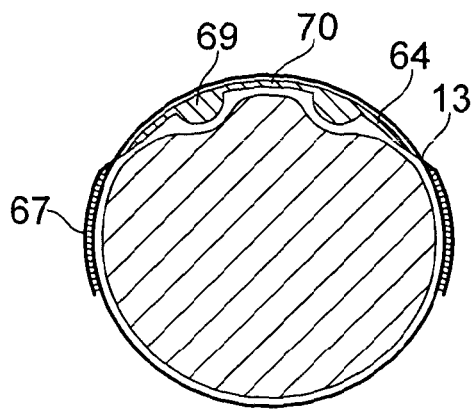
Figure 15B:
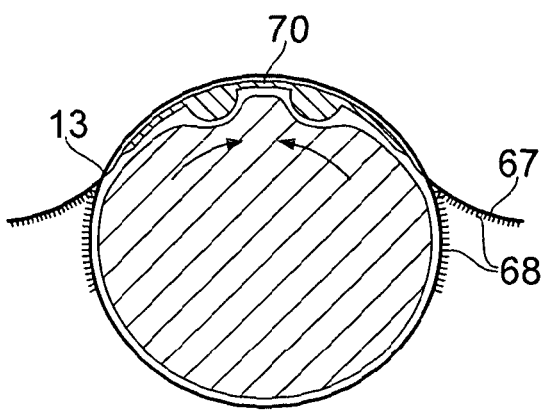
Figure 15C:
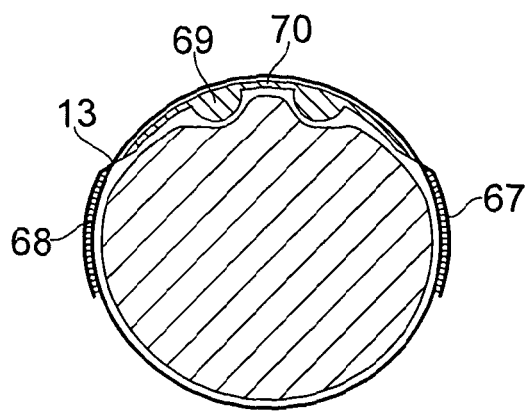
Figure 16B:
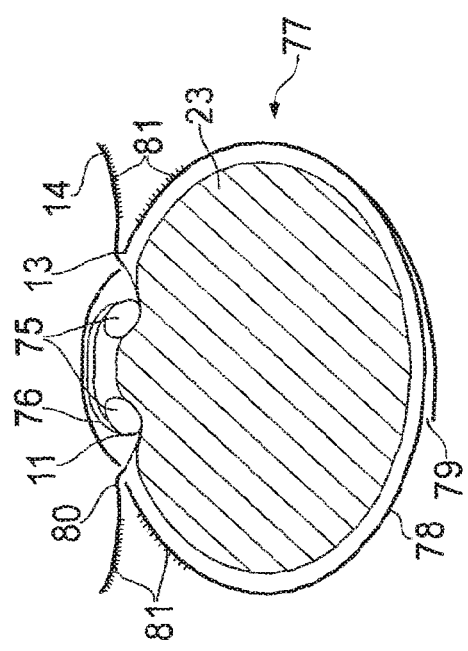
Figure 16C:
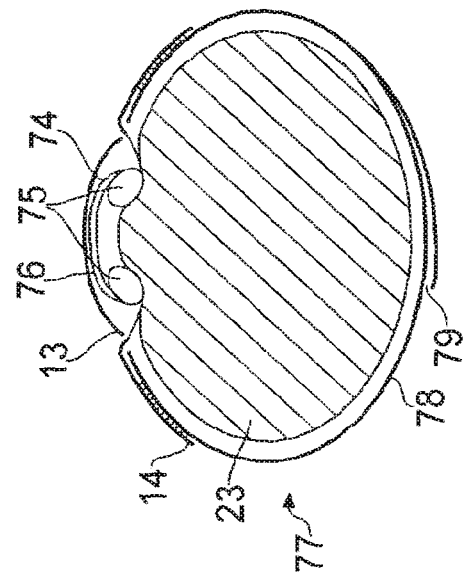
Figure 16A:
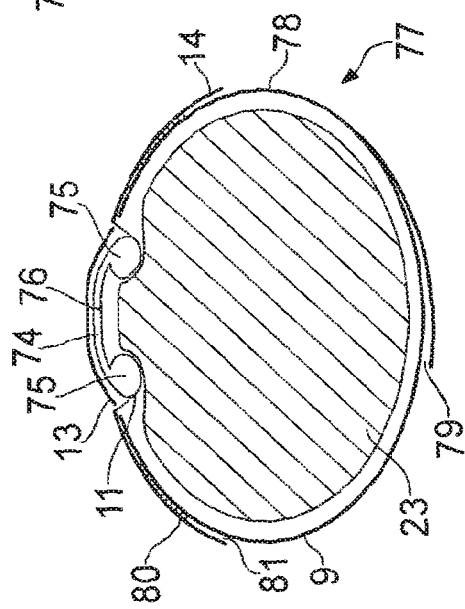
Figure 17:
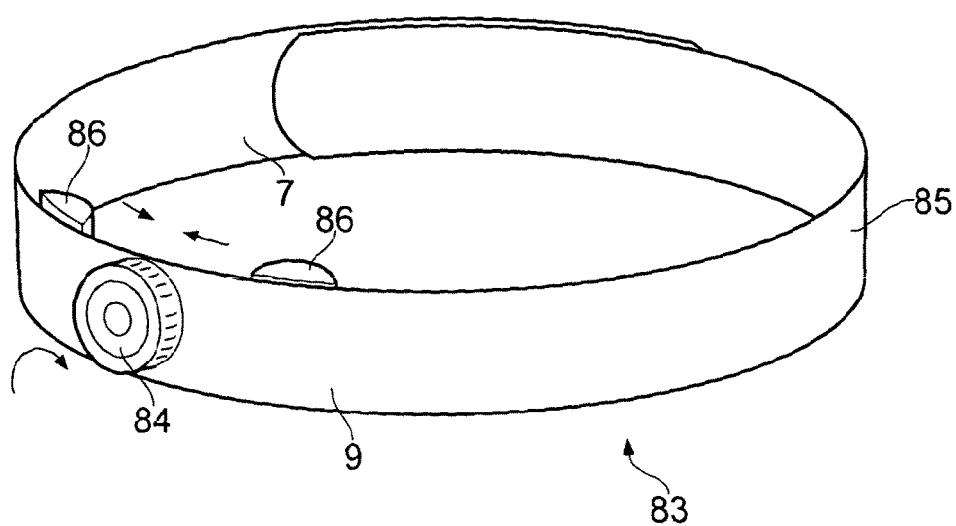
Figure 18:
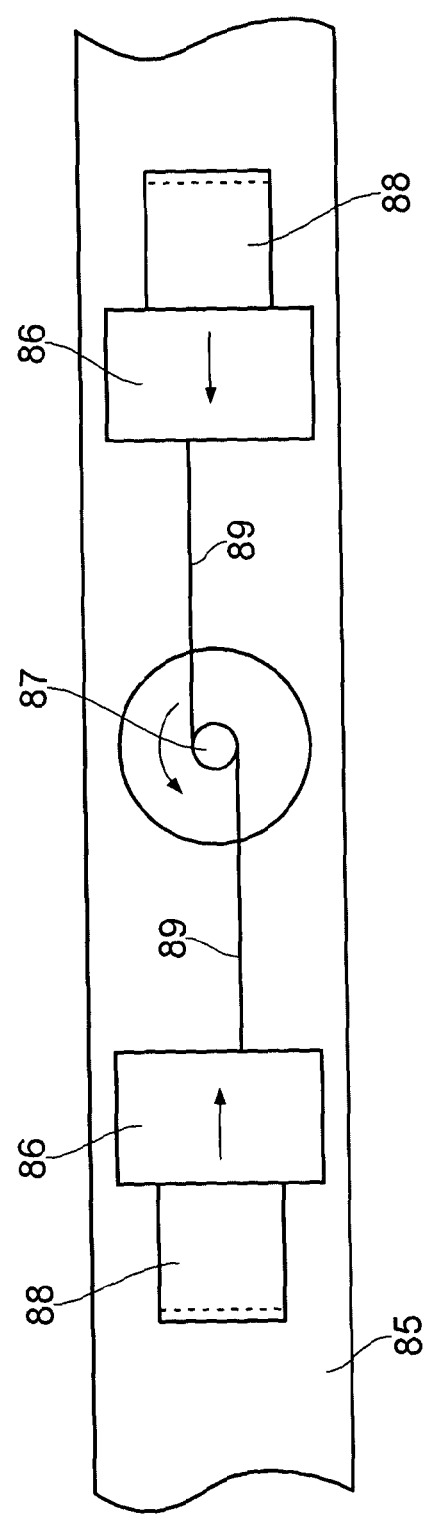
Figure 19:
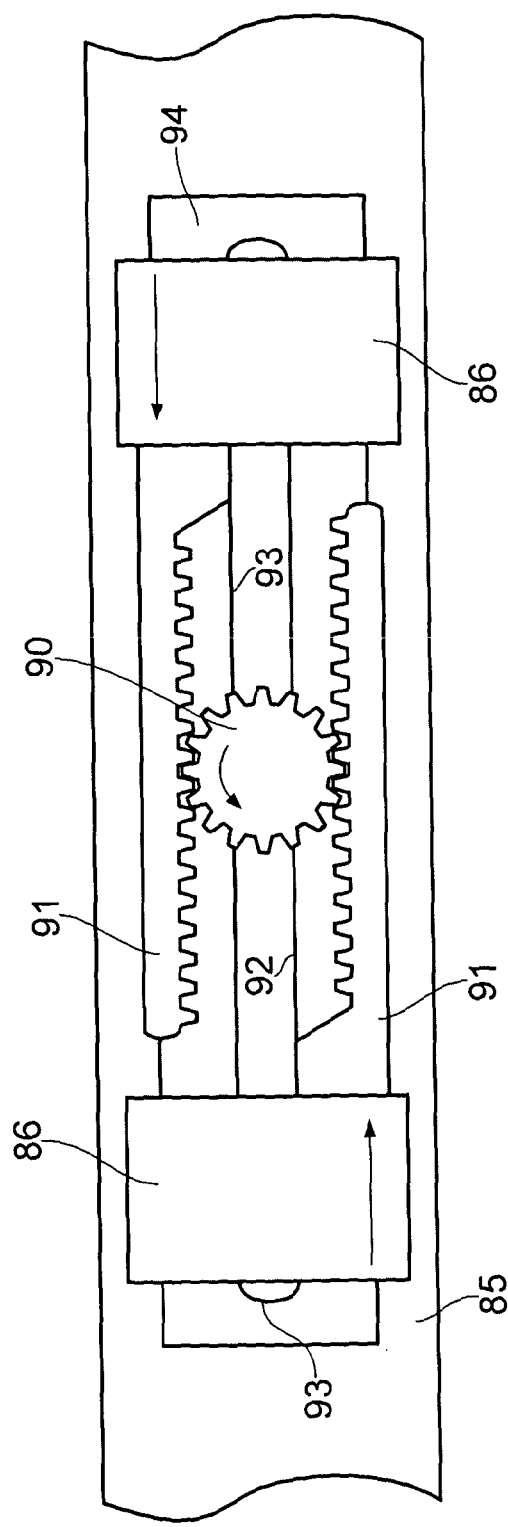
Figure 20:
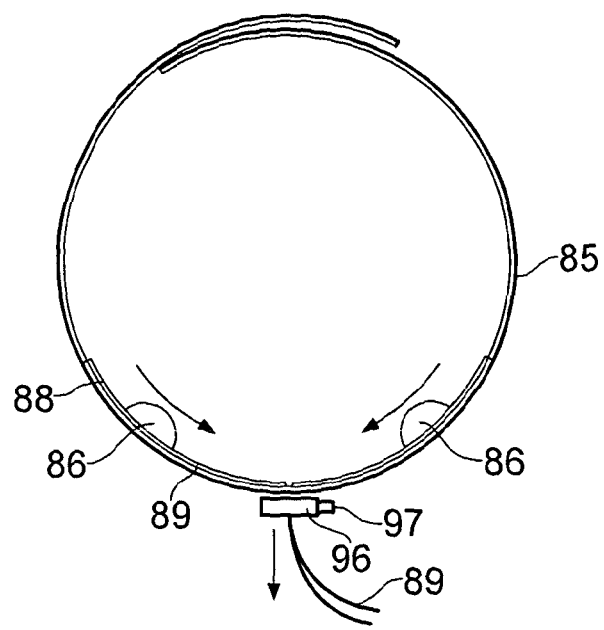
Figure 21:
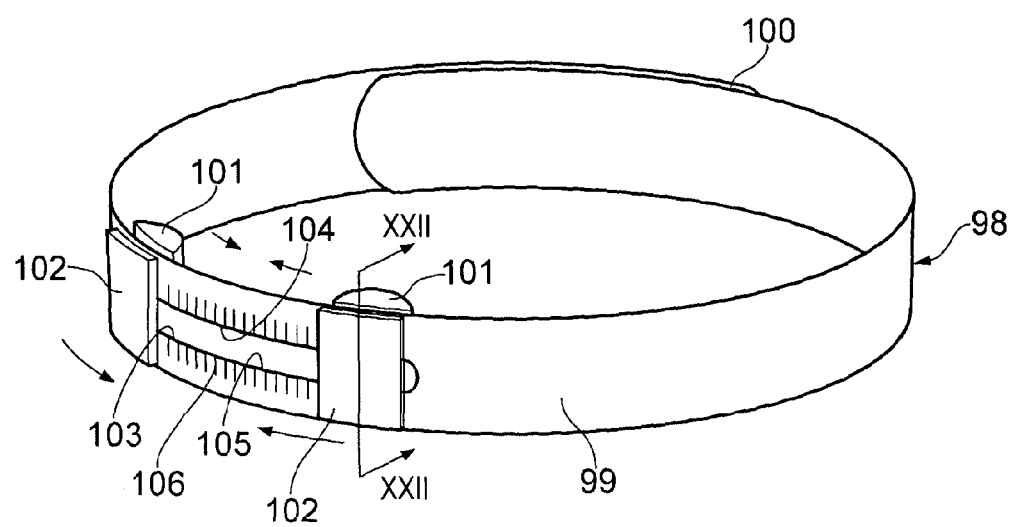
Figure 22:
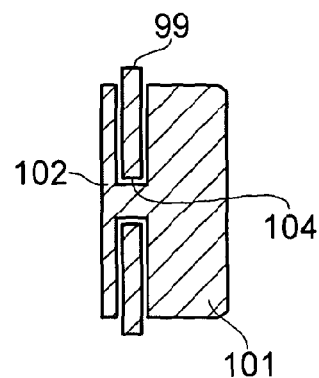
Figure 23:
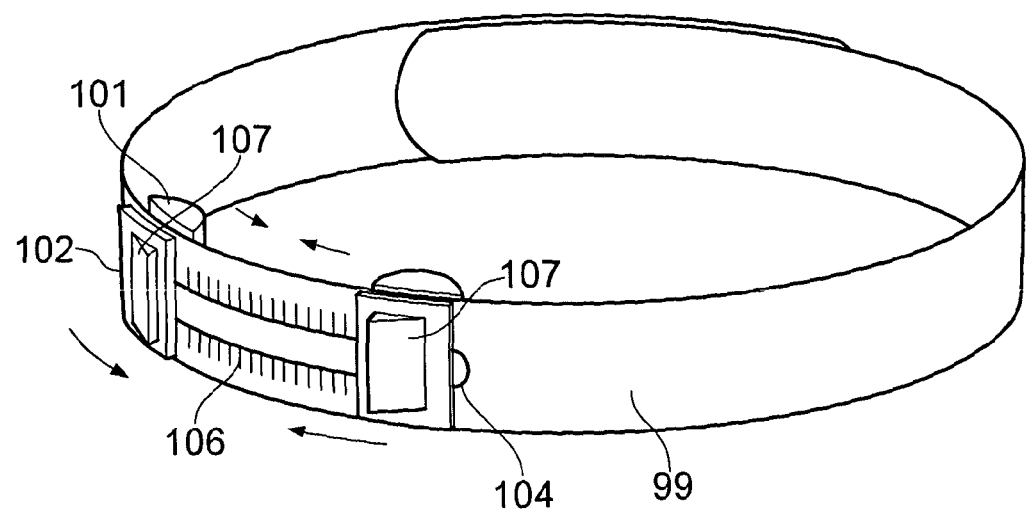
Figure 25:
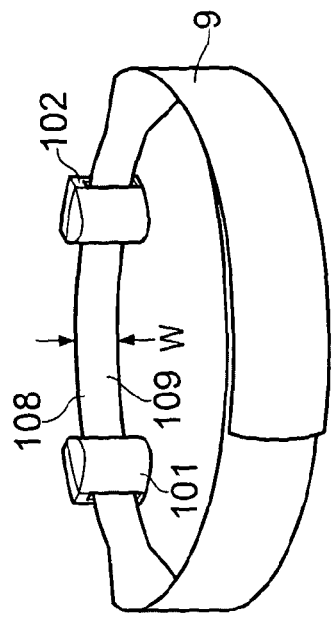
Figure 24:
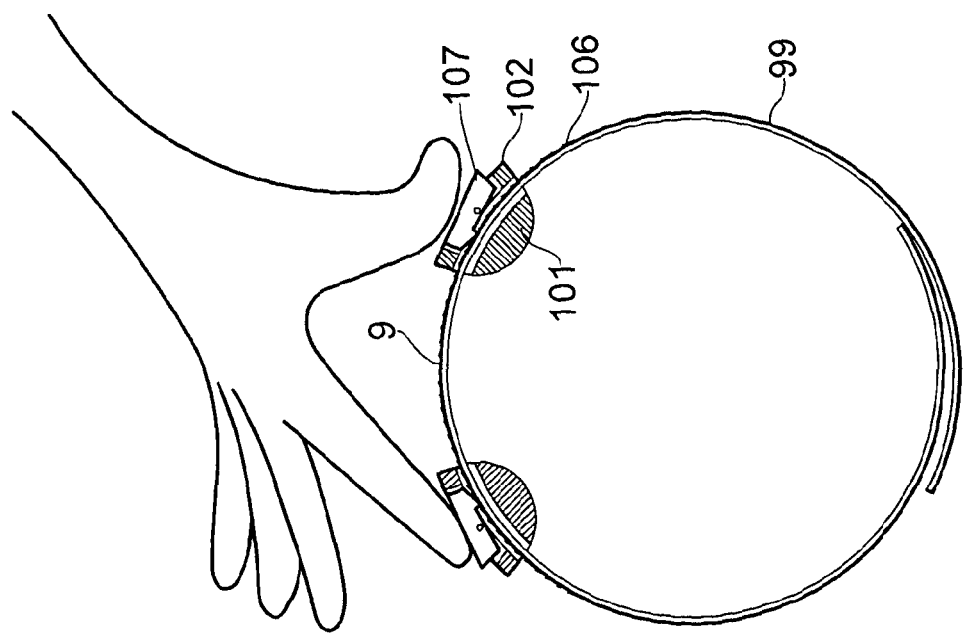
Figure 26:
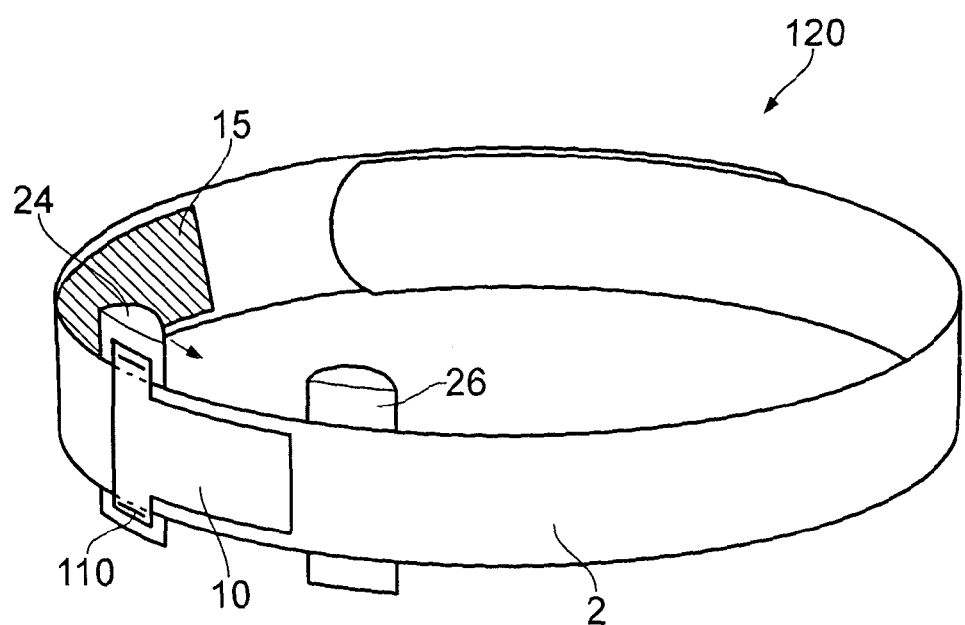
Figure 27:
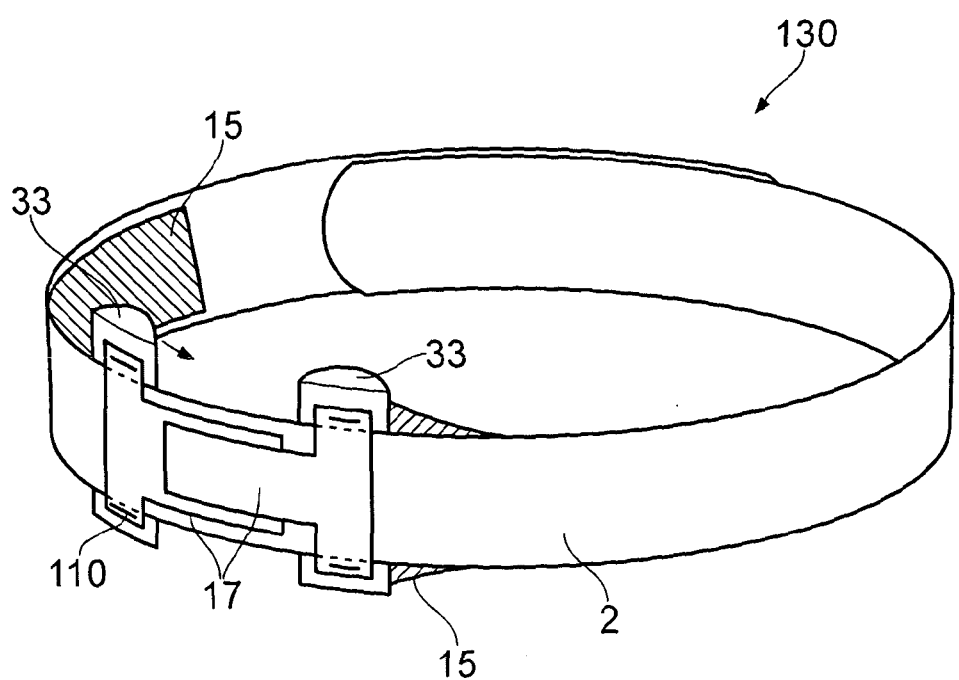

FIGS. 6 and 7 are sectional views similar to FIGS. 2 and 3, showing the lumbar support of FIGS. 4 and 5 in use, before and after fastening of the second bands;

FIG. 8 is a perspective view of a support similar to that of FIG. 1 in which stress offload is achieved by release of the second band;

FIG. 9 is a perspective view of a lumbar support with two second bands in which offloading is achieved by releasing one or both such bands;

FIG. 10 is a perspective view of an embodiment of support with an elastic portion in the first band;

FIG. 11 is a perspective view of a support similar to that of FIG. 10 in which stress is offloaded on release of the second band;

FIGS. 12a, 12b and 12c are sectional views showing successive stages in operation of the support of FIG. 18;

FIGS. 13a, 13b and 13c schematically illustrate alternative embodiments of releasable fastening means employed in the support of FIG. 11;

FIG. 14 is a perspective view of a support with a second band carrying two pads and having an elastic portion between the pads;

FIGS. 15a, 15b and 15c are sectional views showing successive stages in operation of the support of FIG. 14;

FIGS. 16a, 16b and 16c are sectional views showing successive stages in operation of a support incorporating a plastics clip;

FIG. 17 shows a perspective view of an alternative embodiment of support incorporating a manually graspable wheel;

FIG. 18 shows the support of FIG. 17 from the inner first side of the first band illustrating a winding mechanism;

FIG. 19 shows an alternative rack and pinion mechanism for the support of FIG. 17;

FIG. 20 is a schematic illustration of an alternative embodiment of support in which cords are drawn through a toggle to achieve off-loading;

FIG. 21 is a perspective view of a further embodiment of support in which pads are mounted on sliders that run in a slot;

FIG. 22 is a sectional view through the support of FIG. 21, taken along the line XXII-XXII in FIG. 21;

FIG. 23 is a perspective view of a variation of the support of FIG. 22;

FIG. 24 illustrates manual operation of release buttons in the support of FIG. 23;

FIG. 25 is a perspective view of a variation of the support of FIG. 23 in which the first band serves as a rail for sliders carrying pads;

FIG. 26 is a perspective view of another support;

FIG. 27 is a perspective view of yet another support; and

Figure 28:
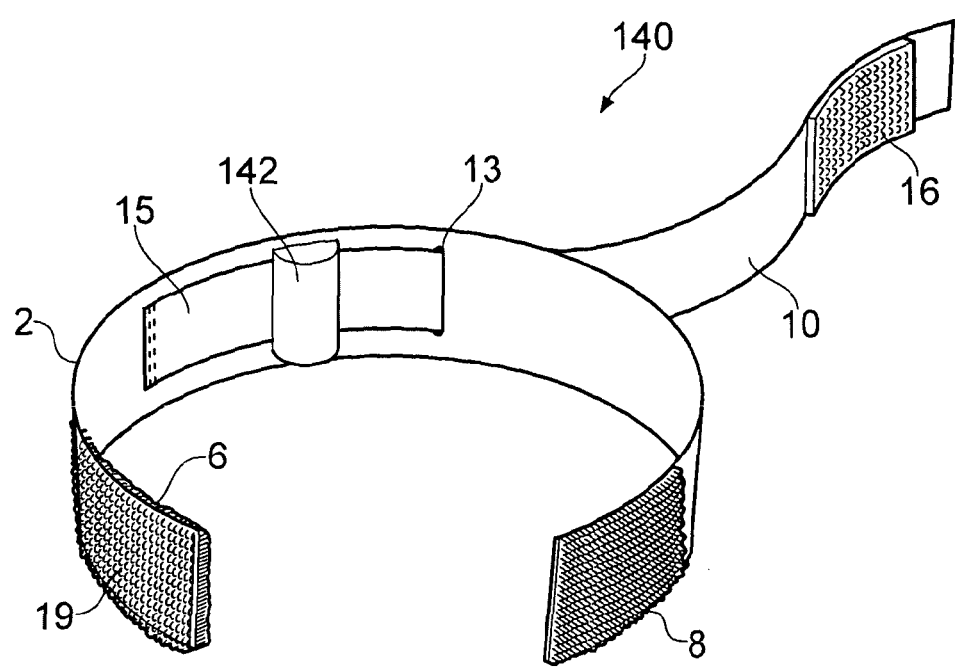

FIG. 28 is a perspective view of a further support.

The support 1 shown in FIG. 1 comprises a first band 2 adapted to pass completely around a human limb to be tightened thereabout with end 3 of band 2 overlapping the other end 4 of band 2 and fastened together by first releasable fastening means 5. Co-operating hook-and-loop fastener pads are readily available under the Velcro® Trademark. As can best be seen in FIG. 1, the releasable fastening means 5 here consists of a hook fastener pad 6 on a first inner side 7 of band 2 adjacent end 3 and a co-operating loop fastener pad 8 on a second outer side 9 of band 2 adjacent end 4. The reverse configuration is equally feasible, as would be other means of releasable fastening such as co-operating hook-and-eye fasteners and co-operating button and buttonholes. However, the use of hook-and-loop fasteners is to be preferred since the fit for different people and for tightness is infinitely adjustable.

The first band may be anatomically shaped to accommodate the curvature of the human or animal body when fitted in position. For example, the first band may have a reduced width for fitting behind a knee of a patient to increase comfort.

A second band 10 has a proximal end 11 fixedly mounted to the first inner side 7 of band 2 at a position 12. The second band 10 passes through a generally slit shaped aperture 13 of band 2 so that distal end 14 of the second band 10 extends outwardly from the aperture. The second band 10 has an elasticated portion 15 adjacent its proximal end 11 which is lengthwise extendible. With the first band 2 tightened about a limb, second band 10 may be pulled, or tensioned, from the external side of band 2 against the bias of its elasticated portion 15 and distal end 14 of the second band 10 may be secured to the second outer side of band 2 by second releasable fastening means 16, here a hook fastener pad 17 on inner side 18 of distal end 14 of second band 10 and a corresponding loop fastener pad 19 on second outer side 9 of band 2 adjacent end 3. FIGS. 2 and 3 illustrate a variation of the FIG. 1 configuration, in which end 4 overlaps end 3, and in which end 3 carries an extended loop fastener pad 20 on the second outer side of band 2 to which respective hook fastener pads 21 and 22 associated with end 4 on inner side 7 of band 2 and with the distal end 14 of second band 10 releasably fasten.

In the embodiments of FIGS. 1 to 3, first band 2 is tightened about a limb or joint 23, as shown in FIG. 2. A first pad 24 mounted on inner side 25 of second band 10 and a second pad 26 fixedly mounted on inner side 7 of first band 2 on the opposite side of aperture 13 from the first pad both engage underlying soft tissue. Drawing out the distal end 14 of second band 10 against the bias of elasticated portion 15 moves the first pad 24 towards the second pad 26 drawing soft tissue with it and so relieving or off-loading stress in the soft tissue between the two pads. The distal end 14 of second band 10 is then secured by the second releasable fastening means to maintain this off-loading.

The spacing between the pads 24, 26 is decreased when the first band has been fixed around the trunk or a joint or limb. That is, pressure is applied between the pads only after the first pad has been fixed in place. In known designs, pads are supported by a single band adjustment of the single band causes pressure to be applied between the pads. An advantage of the present arrangement as described herein is that the first band can be fixed in place to provide a firm base for the second band, and then the second band operated to change the spacing of the pads independently from the first band. This two step process allows the pads to be positioned more accurately at the required locations of the body. Additionally, the two step process is more easily performed by a person, particularly if the person is attaching the support to part of his or her own body, when for example attachment to the elbow allows the use of only one hand.

The use of hook-and-loop fasteners allows infinite adjustment in fitting of first band 2 around a limb or joint. Selection of the required degree of off-loading is even simpler, since distal end 14 of second band 10 may be drawn out against the bias of elasticated portion 15 to the required extent and simply fastened to the second outer side 9 of first band 2 using one hand.

The first band 2 may be constructed from materials commonly employed for conventional braces. Thus, first inner side 7 of first band 2 is suitably a material that can grip the skin without being uncomfortable or excessively sweaty. A fine piled or brushed wicking fabric is preferred and may have a Neoprene backing for strength. The second outer side 9 of first band 2 is suitably formed from a tough durable material, preferably with around 30% stretch for comfort. A suitable material is a 2-3 mm thick double-backed Neoprene (polychloroprene) material.

The elasticated portion 15 should allow an extension of around 100-120% to allow a range of off-loading conditions. A suitable material is woven cotton or polyester covered latex elastic. The pads 24 and 26 need to apply pressure to the soft tissue with which they are in contact in order to achieve off-loading, and are preferably made of a material that will mould to the shape of the skin surface. A suitable material is medical grade silicone resin. Edging tape is suitably employed to finish the edges of aperture 13 and avoid friction with second band 10, which is suitably formed of polyester webbing. It will readily be appreciated that the pads may be differently shaped, and that there may be additional such pads.

Many other alternative configurations to those of support 1 are possible, as explained below. Where appropriate like reference numerals are employed for like feature to those of the supports of FIGS. 1 to 3.

FIGS. 4 to 7 illustrate a support 27 suitable for the lumbar region. The materials employed for the support are suitably the same as those discussed above in relation to the supports of FIGS. 1 to 3. Support 27 has a first band 2, in which end 4 overlaps end 3 and is fastened by first releasable fastening means 5 around the front of a user's trunk 28. Two second bands 29 are employed, the proximal ends 11 of which are fixedly mounted to the first inner side 7 of band 2 at positions 12 on either side of a wide aperture 30 through which the two second bands 29 extend in an interleaved configuration 31. Respective inner sides 18 of the respective distal ends 14 of the second bands 29 mount hook fastener pads 17 adapted for releasable coupling with respective loop fastener pads 19 mounted on second outer side 9 of first band 2 at positions 32 at the sides of the user's trunk in use.

Each second band 29 has an elasticated portion 15 adjacent its proximal end 11. Each second band 29 mounts a pad 33 similar to first pad 24 in the supports of FIGS. 1 to 3.

Lumbar support 27 is easy to fit and to adjust by a user. The support itself is passed around the trunk and fastened at the front in the manner of a belt or conventional lumber brace. The user may then reach around their body to grasp the respective distal ends 14 of second bands 29, pulling these together to the required extent against the bias of elasticated portions 15, causing the respective pads 33 to move towards each other in contact with the soft tissues of the back, to offload stress on the lumbar region between the pads. The respective distal ends 14 are then fastened at the sides of the body to maintain the selected degree of off-loading.

Although support 27 is described as a lumbar support, supports of smaller size but similar configuration may be employed for a lower limb, as the user will have two hands available for fitting and adjusting them.

All of the supports described heretofore rely for their effective off-loading upon drawing out one or more second bands after first securing the first band, and then securing the distal end(s) of the second band(s). The converse arrangement is feasible, as will become apparent from consideration of the embodiments of support shown in FIGS. 8, 9 and 11 described below. In this alternative arrangement, prior to fixing the first band, tensioning the outwardly extending portion of the second band extends the elastic portion and increases the spacing between the pads such that the outwardly extending portion can be fixed to the first band with the elastic portion in a tensioned condition. When the first band is fixed to the trunk or a limb or joint, the outwardly extending portion can be unfixed from the first band to allow the elastic portion to contract thereby decreasing the spacing between the pads and applying pressure to the surface of the trunk or a limb or joint.

In FIG. 8 a support 42 somewhat similar to support 1 of FIG. 1 is illustrated. An elasticated portion 15 is provided adjacent proximal end 11 of second band 10, as in FIG. 1 and a first pad 24 is mounted on second band 10. However, in this arrangement, a second pad 43 is fixedly mounted to inner side 7 of first band 2 on the opposite side of proximal end 11 from slit-shaped aperture 13. Accordingly, drawing out distal end 14 of second band 10 increases separation of the two pads 24 and 43 in this support. Off-loading is achieved in support 42, by drawing out distal end 14 and securing it to the outer side of the first band before the two ends 3 and 4 are fastened together around the limb, joint or trunk. Thereafter, release of the second fastening means between the first and second band, will allow the bias in elasticated portion 15 to draw pad 24 towards pad 43 while engaging underlying tissue to relieve or off-load stress.

FIG. 9 shows a lumbar support 44 with two second bands 10 in which off-loading is achieved by releasing the second bands from their releasable fastening means. In this arrangement, a common proximal end for the two bands 10 is created by sewing a centre line 45 of an elasticated portion 46 to the inner surface of first band 2, thereby effectively creating separate elasticated portions 15 on either side of centre line 45. Each second band 10 mounts a pad 47, and the respective distal ends 14 of the two second bands 10 extend through respective slit-shaped apertures 13. In this lumber support, the respective distal ends 14 are drawn out and secured to the outer side of first band 2 by releasable fastening means 48. After the two ends 3 and 4 of the first band 2 are secured about the trunk of a user, the second fastening means are released allowing the bias in the respective elasticated portions 15 to draw in the second bands to draw pads 47 towards each other to relieve or off-load stress in the lumbar region between them.

In the arrangements of FIGS. 8 and 9, rather than leaving the distal ends 14 loose and potentially flapping about, after off-loading the distal ends are resecured to the releasable fastening means.

FIG. 10 illustrates a support 49 in which off-loading can be achieved by manually grasping distal end 14 of a second band from the exterior of a first band without first unfastening the first band, but in which the second band does not extend through an opening to the inner side of the first band. In support 49, an elasticated portion 50 is formed in first band 51. Proximal end 52 of a second band 53 is fixedly mounted to first band 51 on one side of elasticated portion 50 and distal end 54 of second band 53 extends across elasticated portion 50 for fastening to first band 51 by releasable fastening means 55 on the opposite side of elasticated portion 50 from proximal end 52. Respective pads 56 are fixedly mounted to inner side 57 on opposite sides of elasticated portion 50.

In use of support 49, first band 51 is first fastened around a limb 23 of a user by releasable fastening means 58 at its overlapping ends. This will stretch elasticated portion 50. Thereafter, pulling on the distal end 54 of second band 53 and fastening of that distal end across the elasticated portion will reduce separation of the pads 56 in contact with underlying tissue, thereby relieving or off-loading stress in the region between the pads 56.

In this way, the support comprises a first band having first and second end portions with respective fasteners which can be fastened together to fix the band in a loop around the trunk or a limb or joint; at least two pads located inward of the first band for engaging a surface of the trunk or a limb or joint, the first band having an elastic portion between the pads which is lengthwise extendible so that tensioning the elastic portion causes the pads to move away one from another; a rigid spacer having at least one fastening for fastening outwardly to the first band for fixing the spacing between the pads after the elastic portion is tensioned; wherein releasing the second band from the first band when the first band is fixed around a trunk or a limb or joint causes the pads to move towards under the bias of the elastic portion thereby applying pressure to a surface of the trunk or a limb or joint.

FIGS. 11 to 13c illustrate the converse arrangement in a support with an elasticated portion in the first band, in which off-loading is achieved by releasing a second band. The essential difference between the arrangements of FIGS. 10 and 11 is that in FIG. 11, the second band 53' is formed as a rigid spacer 59. In use, the elasticated portion 50 is stretched to the desired extent and distal end 14 of rigid spacer 59 is secured to first band 51 across the elasticated portion 50 from its proximal end 52, as shown in FIG. 12a. First band 51 is then fastened at its ends 60 and 61 about a limb 23 of a user by releasable fastening means 58, whereafter the releasable fastening means holding the distal end 14 of the spacer 59 to the first band 51 are released (FIG. 12b), and the elasticated portion recoils drawing pads 56 in contact with underlying tissue towards each other, thereby relieving or off-loading stress in the region of the limb between the pads. Distal end 14 of rigid spacer 59 may then be resecured to the first band, as shown in FIG. 12c to maintain the degree of off-loading achieved.

FIGS. 13a, 13b and 13c schematically illustrate three different forms of releasable fastening means for the distal end of the spacer. Use of clips (FIG. 13a), teeth adapted to bite into the fabric backing of the first band (FIG. 13b), or Velcro® hook and loop fastener pads (FIG. 13c) is contemplated.

It is not always necessary, in embodiments of support embodying the present teachings that employ the distal end of a second band as the manually graspable means on the external side of a first band fastened about a limb, joint or trunk for adjusting the position of a first pad relative to a second pad on the internal side of the first band and hence the loading it applies to tissue with which the two pads are in contact without undoing the first band or exposing the tissue between the pads to the exterior of the first band, for the proximal end of the second band to be coupled to the first band directly or via an elasticated portion, as will become apparent from consideration of the supports illustrated in FIGS. 14 to 17c.

Rather than employing two separate second bands in a lumbar support, support 62 shown in FIGS. 14 to 15c has a single second band 63, the central portion of which is formed as a silicone resin moulding 64 that passes through a loop 65 mounted on inner side 7 of a first band 66 provided with two slit-shaped through apertures 13 through which respective ends 67 of the second band extend. The ends 67 of the second band 63 and the outer side of first band 66 are provided with releasable fastening means 68, suitably in the form of co-operating hook and loop fastener pads. Silicone resin moulding 64 defines two pads 69 with a thinner elastically stretchable portion 70 of the moulding between them. Pulling the respective ends 67 of the second band stretches portion 70. If the releasable fastening means 68 are coupled together with portion 70 stretched in this way, and first band 66 then fastened across the front of the user's trunk by releasable fastening means 71 between overlapping ends 72 and 73 of first band 66 (FIGS. 14 and 15a), the releasable fastening means 68 may be released, as shown in FIG. 15b, to allow elasticity in the stretched portion 70 to draw pads 69 in contact with underlying tissue towards each other to relieve or off-load stress in the lumbar region. The releasable fastening means 68 may then be resecured (FIG. 15c) to maintain the degree of of-loading achieved.

As shown in FIGS. 16a, 16b and 16c, as an alternative to relief of elastic stretching of a thin stretchable portion integrally formed with the pads as in FIGS. 14 to 15c, relief of elastic deformation of the shape of a moulded plastics clip can be used to relieve or off-load stress. A plastics clip 74 integrally moulded from silicone resin comprises two pads 75 connected by a curved bight portion 76, and is adapted to clip articles or material between the pads by deformation of the shape of the bight portion. In support 77 of FIGS. 16a, 16b and 16c, a first band 78 is adapted to be fastened about a limb 23 of a user by releasable fastening means 79. Before fastening the first band in this way, pads 75 of a clip 74 located on the inner side of the first band are separated by pulling on the distal ends 14 of respective second bands 80, the proximal ends 11 of which are coupled to pads 75. Distal ends 14 pass through respective slit-shaped apertures 13 in first band 78 and are releasably coupled to outer side 9 of first band 78 by releasable fastening means 81, suitably co-operating hook and loop fastener pads. FIG. 16*a* shows the fastened support 77 in this condition. Subsequent release of releasable fastening means 81 allows the deformed clip 74 to move back towards its initial condition with its pads 75 in contact with underlying tissue, as illustrated in FIG. 16*b* to relieve or off-load stress in the region of limb 23 between the pads 75. Distal ends 14 are then resecured to releasable fastening means 81, as shown in FIG. 16*c*, to maintain the degree of off-loading achieved.

In all of the arrangements described heretofore, adjustment of the position of a first pad located on the inner side of a first band and in contact with underlying tissue relative to a second pad also located on the inner side of the first band was adjusted from outside the first band while the first band remained fastened about a limb, joint or trunk and without exposing the pads or tissue with which they are in contact to the exterior, by manually grasping a second band coupled to the first band and pulling upon it and then releasably fastening its distal end to the exterior of the first band or alternatively releasing the second band from releasable fastening to the exterior of the first band, thereby off-loading stress on underlying tissue between the pads. Other arrangements embodying the present teaching, in which manual adjustment of the position of one pad relative to another may be achieved by manually grasping an adjustment means on the outer side of the first band while the first band remains fastened, but which do not employ a second band, are also contemplated; and a number of such arrangements are described below with reference to FIGS. 17 to 25 of the accompanying drawings.

Support 83 mounts a wheel 84 on outer side 9 of a band 85, and mounts two movable pads 86 in its inner side 7 in the arrangement illustrated in FIGS. 17 and 18. The spindle 87 of wheel 84 extends through the band 85, and, as shown in FIG. 18, each pad 86 is coupled to the inner side 7 of band 85 by an elasticated portion 88, and is attached to an elongate flexible member 89, such as a cord or wire, wound about spindle 87. As wheel 84 is turned in one sense, elongate flexible members 89 are wound on to spindle 87 drawing pads 86 towards each other against the bias of elasticated portions 88. In this arrangement, the bias provided by elasticated portions 88 should be too weak to return pads 86 to their original position until band 85 is unfastened.

FIG. 19 shows an alternative mechanism in which a pinion 90 is mounted on the spindle of wheel 84 and respective racks 91 are coupled to pads 86. Rotation of the pinion 90 by turning external wheel 84 in one sense causes the pads 86 to move towards each other along a track 92 defined by an elongate slot 93 formed in a rectangular plate 94. Turning wheel 84 in the opposite sense causes the pads to move away from each other. Suitably, the racks, the pinion and the plate will all be mounted within the thickness of the band 85 so that only pads 86 are exposed on the inner side 7 of the band, the inner surface of the band having a longitudinal slit to accommodate movement of the pads towards and away from each other. The mechanism illustrated in FIG. 19 must be self-lubricating, and sufficiently thin and flexible to allow the band to be fastened about a limb, joint or trunk of a user. The pinion, racks and plate are all suitably formed of Nylon 6 or Nylon 66.

FIG. 20 shows an alternative to use of a wheel in the arrangement of FIGS. 18 and 19. Here the respective cords 89 pass through an opening 95 through band 85 and through a spring loaded releasable toggle 96 of the kind commonly employed for holding drawn adjustment cords in outdoor clothing. Thus, with band 85 fastened about a limb, joint or trunk, pressing on button 97 to release the grip of toggle 96, drawing of cords 89 and then subsequently releasing button 97 so that the toggle operates again, results in the pads 86 being drawn towards each other in contact with underlying tissue to relive or off-load stress between the pads.

Support 98 of FIGS. 21 and 22 has a band 99 adapted to be fastened about a limb, joint or trunk by releasable fastening means 100, as in previous embodiments. Two pads 101 are mounted on sliders 102 so that the respective slider/pad combinations can be manually moved along a track 103 defined by a groove 104 extending through the band 99. The sliders 102 may be manually pushed towards each other in contact with underlying tissue after the band 99 has been fastened about a limb, joint or trunk to relive or off-load stress in the tissue between the pads. To resist the sliders 102 simply sliding back to their original positions, edges 105 of groove 104 are provided with friction or grip features or a simple ratchet 106, serving to resist movement of the sliders 102.

The sliders 102 may be provided with finger release buttons 107 for locking with or release from the ratchet portions 106, as shown in FIGS. 23 and 24.

Rather than employing sliders 102 that move along a groove 104, as in FIG. 29 or 31, a portion 108 of the band 99, preferably with a reduced width W may serve as a rail 109 over and along which the sliders 102 may travel, as illustrated in FIG. 25. The outer surface 9 of band 99 is suitably formed with teeth forming a ratchet along portion 108, and the sliders 102 may incorporate buttons, as in the arrangement of FIGS. 23 and 24.

The ratchets 106 in the arrangements of FIGS. 21 to 25 are suitably integrally moulded into respective thin plastics plates formed of flexible Nylon and mounted in the band 99, and which additionally define the edges of the groove 104 in the arrangements of FIGS. 21 to 24.

FIG. 26 shows a support 120 for the trunk or a limb or joint of a human or animal. Support 120 is modified from the arrangements previously described in that the movable pad 24 fixed to the second band 10 and the fixed pad 26 fixed to the first band 2 extend laterally beyond the width of the first band. As previously discussed, this arrangement allows a user to see the position of the pads so that the pads can be accurately positioned with respect to the affected body surface portion when the first band is fixed in place. The outwardly extending portion 10 of the second band is fixed by suitable fastenings 110 to lateral extensions of the movable pad providing an adjustment means which extends from an inner side to an outer side of the first band to allow operation outwardly of the first band when the first band is fixed. This configuration is an alternative to the provision of an aperture (e.g. aperture 13 in FIGS. 1 to 3).

FIG. 27 shows a support 130 for the trunk or a limb or joint of a human or animal. Support 130 is similar to the support 120 shown in FIG. 26 except that the first and second bands 33 are both movable and fixed to respective second bands 29. The second bands have elastic portions 15 which allow the spacing between the pads to be changed when outwardly extending portions 17 of the second pads are tensioned by pulling and when the first band is fixed in place.

FIG. 28 shows a support 140 for the trunk or a limb or joint of a human or animal comprising a single pad for applying pressure to a body surface portion. In this configuration, the offloading applied to a muscle, tendon or ligament for example is asymmetric relative to a nominally central longitudinal line of body portion. In certain anatomical or physiological conditions, it may be preferred or acceptable to apply asymmetric offloading with a single pad. It will be appreciated that although support 140 comprises only a single pad it is similar to other embodiments described above and therefore those aspects which are similar will not be described again for brevity.

The pad 142 is located inwardly of the first band 2 for engaging the surface portion of the trunk or a limb or joint. The second band 10 has a portion located inwardly of the first band on which the pad 142 is supported for movement independently of the first band when the first band is fixed in place. The adjustment means in this arrangement comprises a portion of the second band 10 which through an aperture 13 from inner side to an outer side of the first band 2 to allow operation outwardly of the first band when the first band is fixed for adjusting the position of the pad 142. Tensioning the outwardly extending portion by pulling moves the pad 142 relative to the first band to apply asymmetric offloading to a body surface portion.

As will be appreciated by those skilled in the art, embodiments of the invention described herein allow subcutaneous muscular, tendinous, fascial, neural, vascular tissue to be picked up, gathered, or lifted facilitating better interfacing of the tissue as well as improving local blood flow. Additionally the muscular/tendon complex is mechanically lengthened which unloads stress from a specific injury site along its length or at its point of attachment to the bone. Further to a mechanical lengthening effect there may be an inhibitory effect (i.e. it prevents the muscle/tendon complex working to the extent where it could cause further injury to itself). This latter effect would be particularly useful in instances where tissues are held in tension for long periods of time, for example working in prolonged static positions, particularly tissue held against gravity.

Taping can also be used directly to reduce discomfort by unloading irritated/inflamed (therefore swollen) tissues and creating more space around the site and therefore reducing pressure. It also may enhance the dissipation of effusion (the fluid resulting as a by-product of inflammation) which, if left in situ can also create pressure and lead to the development of scar tissue.

The single pad embodiment described with reference to FIG. 28 pulls tissue to one side producing at least partially the same therapeutic effect as the two pad embodiments, particularly if applied where anatomy is such that it causes a bunching of tissue (e.g. it pulls up to a boney margin which effectively creates the same effect as a second pad). With this type of taping there can also be a change in the angulation of the muscle/tendon complex which can alter the direction of forces leading to a reduction in symptoms, irritation, or inflammation of tissue.

Offload taping can be used as a treatment approach in it's own right and/or as a supplementary treatment to maintain the effects of treatment between physiotherapy sessions. It can also be used as a diagnostic tool. i.e. if a physiotherapist carries out a 'tennis elbow' test on a patient which proves positive, taping can be applied and the test re-performed. If the test proves less positive or negative then tendinitis/epicondylitis is further confirmed and a taping regime may well prove to be beneficial.

The invention claimed is:

1. A support for a body part of a human or animal comprising:
a first band configured to at least partially encompass the body part, the first band having a first end portion, a second end portion, an inner side extending along a length between the first and second end portions and configured to face toward the body part, an outer side extending along the length opposite the inner side and configured to face away from the body part, and an aperture surrounded by the first band and disposed along the length between the first and second end portions, the aperture configured to extend through the first band from the inner side to the outer side;
at least one pad located inwardly of the first band, the at least one pad being configured to engage the body part;
a second band having a fixed portion non-removably attached to the inner side of the first band, and an inward portion located inwardly of the first band and configured to support the at least one pad, the inward portion configured for movement independently of the first band to apply pressure to the body part with the at least one pad; and
adjustment means connected to or formed by an adjustment portion of the second band, the adjustment means extending through the aperture in the first band from a location inwardly of the first band to a location outwardly of the first band to allow operation outwardly of the first band to adjust the pressure exerted by the at least one pad on the body part.

2. The support as claimed in claim 1, wherein the first and second end portions of the first band have respective fasteners configured to be fastened together for fixing the band relative to the body part; and wherein the second band comprises an elastic portion which is lengthwise extendible to allow movement of the at least one pad by operation of the adjustment means when the first band is fixed in position.

3. The support as claimed in claim 1, wherein the adjustment means is formed by the adjustment portion of the second band having an outward portion extending outwardly from the inner side to the outer side of the first band that can be tensioned to adjust the position of the at least one pad, the outward portion comprising a fastening for fastening to the first band for fixing the position of the at least one pad after tensioning.

4. The support as claimed in claim 3, wherein the support is configured such that tensioning the outward portion of the second band extends an elastic portion causing movement of the at least one pad and configured to apply pressure to the body part.

5. The support as claimed in claim 3, wherein the support is configured such that prior to fixing the first band, tensioning the outward portion extends an elastic portion and causes movement of the at least one pad such that the outward portion can be fixed to the first band with the elastic portion in a tensioned condition, and wherein when the first band is fixed relative to the body part, the outward portion can be unfixed from the first band to allow the elastic portion to contract thereby causing movement of the at least one pad to apply pressure to the body part.

6. The support as claimed in claim 1, wherein the at least one pad includes a first pad and a second pad, wherein the second band supports the second pad inwardly of the first band for movement relative to the first band, and the adjustment means comprises a second outwardly extending portion for extending from the second band from the inner side to the outer side of the first band to allow operation outwardly of the first band when the first band is fixed relative to the body part for adjusting the spacing between the first and second pads.

7. The support as claimed in claim 6, wherein the inward portion of the second band includes a first inward portion and a second inward portion; wherein the first inward portion of the second band supports the first pad, and the second inward portion of the second band supports the second pad;

wherein the adjustment means is formed by the adjustment portion of the second band having a first outward portion extending outwardly from the inner side to the outer side of the first band that can be tensioned to adjust the position of the first pad, the first outward portion having a fastening for fastening to the first band for fixing the position of the first pad after tensioning;

wherein the support includes a second adjustment means formed by a second adjustment portion of the second inward portion of the second band, the second adjustment portion having a second outward portion extending outwardly from the inner side to the outer side of the first band that can be tensioned to adjust the spacing between the first and second pads, the second outward portion having a fastening for fastening to the first band and for fixing the spacing between the first and second pads after tensioning.

8. The support as claimed in claim 7, wherein the support is configured such that prior to fixing the first band, tensioning the first outward portion and the second outward portion increases the spacing between the first and second pads such that the first and second outward portions can be fixed to the first band while in a tensioned condition, and wherein when the first band is fixed relative to the body part, the first and second outward portions can be unfixed from the first band to allow contraction thereby decreasing the spacing between the first and second pads and applying pressure to the body part.

9. The support as claimed in claim 1, wherein the at least one pad includes at least two pads located inwardly of the first band and configured to engage the body part, the second band supporting at least one of the pads for movement relative to the other of the pads independently of the first band to apply pressure to the body part between the pads, the adjustment means being operable outwardly of the first band when the first band is fixed relative to the body part for adjusting the spacing between the pads.

10. The support as claimed in claim 9, wherein the at least two pads are connected one to the other by a resilient clip which biases the pads towards each other, and the support is configured such that tensioning the second band causes the pads to move away from one another such that prior to fixing the first band, the second band can be tensioned to move the pads away from each other and the spacing between the pads fixed by fastening ends of the second band to the first band, wherein following fixing of the first band relative to the body part, the second band can be unfastened such that the pads move towards each other under the biasing force of the clip independently from the first band to apply pressure to the body part.

11. The support as claimed in claim 1, wherein the adjustment means comprises a wheel fixed for rotation relative to the first band to cooperate with the second band, wherein rotation of the wheel causes the at least one pad supported by the second band to increase or decrease the pressure exerted on the body part.

12. The support as claimed in claim 1, wherein the adjustment means comprises a cord extending through the aperture, and a clamp for securing the cord relative to the first band when the cord has been tensioned.

13. The support as claimed in claim 1, comprising one or more retainers fixed to the inner side of the first band for limiting movement of the inward portion of the second band relative to the first band in a widthwise direction of the first band.

14. The support as claimed in claim 1, wherein the at least one pad is arranged relative to the first band such that when the first band is fixed relative to the body part the at least one pad remains visible to facilitate positioning of the at least one pad.

15. The support as claimed in claim 1, wherein the at least one pad is detachably mounted to the second band or the first band to allow movement of the at least one pad prior to being configured for fixing the first band relative to the body part and to allow variation of an initial spacing between two or more of the at least one pad.

16. A support for a body part of a human or animal comprising: a first band configured to at least partially encompass the body part, the first band having a first end portion, a second end portion, a length extending between the first and second end portions, an inner side extending along the length and configured to face toward the body part, an outer side extending along the length and configured to face away from the body part, and an aperture surrounded by the first band and disposed along the length between the first and second end portions, the aperture configured to extend through the first band from the inner side to the outer side; at least one pad located inwardly of the first band, the at least one pad being configured to engage the body part; a second band having a fixed portion non-removably attached to the inner side of the first band, and an inward portion located inwardly of the first band and configured to support the at least one pad; and an adjustment component extending through the aperture in the first band from a location inwardly of the first band to a location outwardly of the first band; wherein the adjustment component is configured to permit operation outwardly of the first band to move the inward portion of the second band independently of movement of the first band to adjust pressure exerted by the at least one pad on the body part.

17. The support as claimed in claim 16, wherein the adjustment component is at least partially formed by an adjustment part of the second band, in which the adjustment part of the second band connects with the inward portion of the second band, and in which the adjustment part of the second band has an outward portion extending outwardly from the first band.

18. The support as claimed in claim 16, wherein the adjustment component includes a rotatable wheel configured to cooperate with the inward portion of the second band such that rotation of the wheel increases or decreases pressure exerted by the at least one pad on the body part.

* * * * *